United States Patent
Rosen et al.

(10) Patent No.: US 11,497,435 B2
(45) Date of Patent: Nov. 15, 2022

(54) NON-INVASIVE COLON MOTILITY MONITORING SYSTEM

(71) Applicant: The Children's Mercy Hospital, Kansas City, MO (US)

(72) Inventors: John M. Rosen, Fairway, KS (US); Francisco M. Vargas-Luna, Leon (MX)

(73) Assignee: The Children's Mercy Hospital, Kansas City, MO (US)

( * ) Notice: Subject to any disclaimer, the term of this patent is extended or adjusted under 35 U.S.C. 154(b) by 67 days.

(21) Appl. No.: 16/639,840

(22) PCT Filed: Aug. 17, 2018

(86) PCT No.: PCT/US2018/046881
§ 371 (c)(1),
(2) Date: Feb. 18, 2020

(87) PCT Pub. No.: WO2019/036596
PCT Pub. Date: Feb. 21, 2019

(65) Prior Publication Data
US 2020/0253535 A1    Aug. 13, 2020

Related U.S. Application Data

(60) Provisional application No. 62/547,542, filed on Aug. 18, 2017.

(51) Int. Cl.
*A61B 5/00* (2006.01)
*A61B 5/053* (2021.01)
*A61B 5/392* (2021.01)

(52) U.S. Cl.
CPC .......... *A61B 5/4255* (2013.01); *A61B 5/0022* (2013.01); *A61B 5/053* (2013.01);
(Continued)

(58) Field of Classification Search
CPC ..... A61B 5/4255; A61B 5/392; A61B 5/0022; A61B 5/053; A61B 5/6804; A61B 5/7246
See application file for complete search history.

(56) References Cited

U.S. PATENT DOCUMENTS 5,503,157 A    4/1996 Sramek
5,529,072 A    6/1996 Sramek
(Continued)

FOREIGN PATENT DOCUMENTS

JP    2002-519089    7/2002
JP    2004-000138    1/2004
(Continued)

OTHER PUBLICATIONS

Supplementary Search Report in corresponding European Patent Application Serial No. 18846142.0, dated Apr. 20, 2021.
(Continued)

*Primary Examiner* — Daniel L Cerioni
(74) *Attorney, Agent, or Firm* — Hovey Williams LLP

(57) ABSTRACT

A non-invasive colon motility monitoring system comprises an electrobioimpedance unit, an electromyography unit, and a computing device. The electrobioimpedance unit measures an impedance of a body of a subject and communicates an impedance signal that varies according to the measured impedance. The electromyography unit measures an electric voltage of the body of the subject and communicates a voltage signal that varies according to the measured voltage. The computing device includes a processing element programmed to receive the impedance signal and determine impedance data from the impedance signal, receive the voltage signal and determine voltage data from the voltage signal, compute impedance derivative data from the impedance data, compute a correlation between any two of the impedance data, the voltage data, and the impedance derivative data, determine when a bowel event is about to occur
(Continued)

based on the correlation, and provide an indication of the bowel event.

16 Claims, 13 Drawing Sheets

(52) U.S. Cl.
CPC ............ *A61B 5/392* (2021.01); *A61B 5/6804* (2013.01); *A61B 5/7246* (2013.01)

(56) References Cited

U.S. PATENT DOCUMENTS

| | | | |
|---|---|---|---|
| 5,704,368 | A | 1/1998 | Asano et al. |
| 6,251,681 | B1 | 6/2001 | Davies et al. |
| 7,569,019 | B2 | 8/2009 | Bour et al. |
| 7,593,768 | B1 | 9/2009 | Vasiliev et al. |
| 9,445,742 | B2 | 9/2016 | Slizynski et al. |
| 9,943,264 | B2 | 4/2018 | Axelrod et al. |
| 2010/0100146 | A1 | 4/2010 | Blomqvist |
| 2010/0228105 | A1* | 9/2010 | Policker ................. A61B 5/392 600/302 |
| 2012/0277619 | A1 | 11/2012 | Starkebaum et al. |
| 2013/0150749 | A1 | 6/2013 | McLean et al. |
| 2014/0275748 | A1 | 9/2014 | Dunki-Jacobs et al. |
| 2015/0148619 | A1 | 5/2015 | Berg et al. |
| 2016/0338634 | A1 | 11/2016 | Neu et al. |
| 2017/0128722 | A1* | 5/2017 | Perez .................. A61B 5/4836 |
| 2017/0202503 | A1 | 7/2017 | Nakanishi et al. |
| 2019/0001135 | A1* | 1/2019 | Yoo ...................... A61N 1/3603 |
| 2019/0076380 | A1 | 3/2019 | Baron et al. |
| 2019/0358450 | A1* | 11/2019 | Lo ............................ A61N 1/36 |

FOREIGN PATENT DOCUMENTS

| | | |
|---|---|---|
| WO | 2000-000082 | 1/2000 |
| WO | 2016057244 | 4/2016 |
| WO | 2016187456 | 11/2016 |

OTHER PUBLICATIONS

Li, et al., "Gastric motility functional study based on electrical bioimpedance measurements and simultaneous electrogastrography", J Zhejiang Univ-Sci B (Biomed & Biotechnol), 2011, 12(12), pp. 983-989.

Smout, et al., "Gastrointestinal motility testing", Best Practice & Research Clinical Gastroenterology, 2009, 23, pp. 287-298.

Huerta-Franco, et al., "Use of short-term bio-impedance for gastric motility assessment", Medical Engineering & Physics, 2009, 31, pp. 770-774.

International Search Report and Written Opinion in corresponding PCT/US2018/046881, dated Jan. 9, 2019.

G-Tech Medical, "An EKG for the GUT", http://www.gtechmedical.com accessed on May 29, 2018.

Notice of Reasons for Refusal in corresponding Japanese Patent Application No. 2020-508373, dated Jun. 13, 2022 (English translation attached).

* cited by examiner

FRONT VIEW

REAR VIEW

NON-INVASIVE COLON MOTILITY MONITORING SYSTEM

CROSS-REFERENCE TO RELATED APPLICATIONS

The present application is the U.S. National Stage of International Patent Application No. PCT/US2018/046881, filed Aug. 17, 2018, which claims the priority benefit of U.S. Provisional Patent Application Ser. No. 62/547,542, filed Aug. 18, 2017, entitled NON-INVASIVE COLON MOTILITY MONITORING SYSTEM, each of which is incorporated by reference in its entirety herein.

BACKGROUND OF THE INVENTION

Field of the Invention

Embodiments of the current invention relate to non-invasive systems for monitoring colon activity based upon electrical bioimpedance measurements.

Description of Related Art

Bowel and continence issues affect both children and adults, and many patients who seek help will initially fail non-surgical or non-medical therapy. Issues such as constipation, irritable bowel syndrome, fecal incontinence can be debilitating for the patient and caregivers, leading to poor quality of life, depression, and behavioral issues. In addition, untreated disorders can give rise to chronic conditions and other physical effects. As many as one-third of all children under the age of 9 will experience constipation with no identified underlying cause. Constipation and other bowel irregularities are also often encountered during toilet training of children. Further, bowel irregularities can also arise as a secondary effect of other conditions or events, such as surgery, aging, labor and delivery, disease, or other underlying neuromuscular disorders, etc. Unfortunately, current methods for investigating and monitoring bowel activity to assess underlying conditions and causes and assess treatment options require invasive techniques that require an internally placed catheter. In short, it is currently difficult and invasive to clarify the pathophysiology of an ongoing bowel irregularity. In addition, less invasive techniques for general monitoring of colon function include merely listening to the abdomen with a stethoscope, providing very little actual information regarding the subject's status.

Thus, there remains a need for less invasive techniques for monitoring colon activity that would be useful both for the purpose of investigating acute or chronic medical conditions and bowel dysfunctions where detailed information may be desired, as well as general-purpose colon activity assessment, such as in toilet training.

SUMMARY OF THE INVENTION

Embodiments of the current invention solve the above-mentioned problems and provide a distinct advance in the art of non-invasive colon motility monitoring. Various embodiments of the current invention provide a system that measures an electrobioimpedance Z and an electromyography voltage of a body of a subject in a colorectal region. Processing of signals that include the measurements provide information that can be used to determine a "bowel event," which is used herein to refer to colonic contractions indicative of an imminent bowel movement in the subject.

An embodiment of the system comprises an electrobioimpedance unit, an electromyography unit, and a computing device. The electrobioimpedance unit is configured to measure an impedance of a body of a subject in a colorectal region and communicate an impedance signal that varies according to the measured impedance. The electromyography unit is configured to measure an electric voltage of the body of the subject in the colorectal region and communicate a voltage signal that varies according to the measured voltage. The computing device includes a processing element configured or programmed to receive the impedance signal and determine impedance data from the impedance signal, receive the voltage signal and determine voltage data from the voltage signal, compute impedance derivative data from the impedance data, compute a correlation between any two of the impedance data, the voltage data, and the impedance derivative data, determine when a bowel event is about to occur based on the correlation, and provide an indication of the bowel event.

Another embodiment of the current invention provides a non-invasive colon motility monitoring system comprising an electrobioimpedance unit, an electromyography unit, an article of clothing, and a computing device. The electrobioimpedance unit is configured to measure an impedance of a body of a subject in a colorectal region and communicate an impedance signal that varies according to the measured impedance. The electromyography unit is configured to measure an electric voltage of the body of the subject in the colorectal region and communicate a voltage signal that varies according to the measured voltage. The computing device includes a processing element configured or programmed to receive the impedance signal and determine impedance data from the impedance signal, receive the voltage signal and determine voltage data from the voltage signal, compute impedance derivative data from the impedance data, compute a correlation between any two of the impedance data, the voltage data, and the impedance derivative data, determine when a bowel event is about to occur based on the correlation, and provide an indication of the bowel event.

Yet another embodiment of the current invention provides an array of colon motility monitoring electrodes comprising four current electrodes, four voltage electrodes, and three electromyography (EMG) electrodes. The current electrodes are configured to be electrically connected to an electric current source of an electrobioimpedance unit and are positioned to form a first quadrilateral. The voltage electrodes are configured to be electrically connected to an electric voltage meter of the electrobioimpedance unit. The voltage electrodes are positioned to form a second quadrilateral that is smaller in one dimension than the first quadrilateral and located within the first quadrilateral such that a first pair of current electrodes is generally aligned with a first pair of voltage electrodes to form a first impedance measurement group and a second pair of current electrodes is generally aligned with a second pair of voltage electrodes to form a second impedance measurement group. The EMG electrodes are configured to be electrically connected to an electric voltage meter of an EMG unit. First and second EMG electrodes are positioned in general alignment with either the first impedance measurement group or the second impedance measurement group such that each EMG electrode is positioned at an opposing end of either impedance measurement group. A third EMG electrode is positioned in the vicinity of either the first or second EMG electrodes.

Other embodiments of the current invention provide a system generally including a first set of electrodes placed on the skin for applying an electrical current in the pelvic region of the subject, wherein the first set of electrodes applies current in a configuration that generates an electrical field centered over the colon of the subject, and a second set of electrodes positioned on the skin within the perimeter of the electrical field measures voltage changes across the field. The impedance values (Z) are calculated from the measured voltage and change in voltage over time (dZ/T). The system further includes a third set of electrodes for measuring electrical signals from musculoskeletal movements of the subject, and specifically internal movements in the pelvic region. A comparison of impedance values to EMG signals over time is indicative of colon activity.

Colon activity that is intrinsic (e.g., contraction of colonic smooth muscle) is characterized by high correlation between mean EMG and impedance (Z) signals, with concurrent low correlation between Z and dZ/dt. Under these conditions, the system would indicate a primary "positive result". A bear down maneuver (described as internal pushing), also seems to show high correlation between mean EMG and Z, but no change in the correlation between Z and dZ/dt compared to rest or other conditions. This could be a secondary "positive result" as the subject may be attempting defecation in response to urge/desire.

Methods of using the system in a variety of manners are also described. Methods include monitoring colon activity for toilet training, post-operative monitoring, medical intervention for bowel irregularities, and the like. Methods for use of the system in pets and other non-human animals are also described. The methods generally comprise placing the electrodes of the system in the desired configuration, as described herein, activating the electric current, and reviewing output data or information provided by the system. Such data may include detailed information regarding waveforms, or may simply be a positive or negative indicator of colon activity.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the current invention are described in detail below with reference to the attached drawing figures, wherein.

Figure 17A:
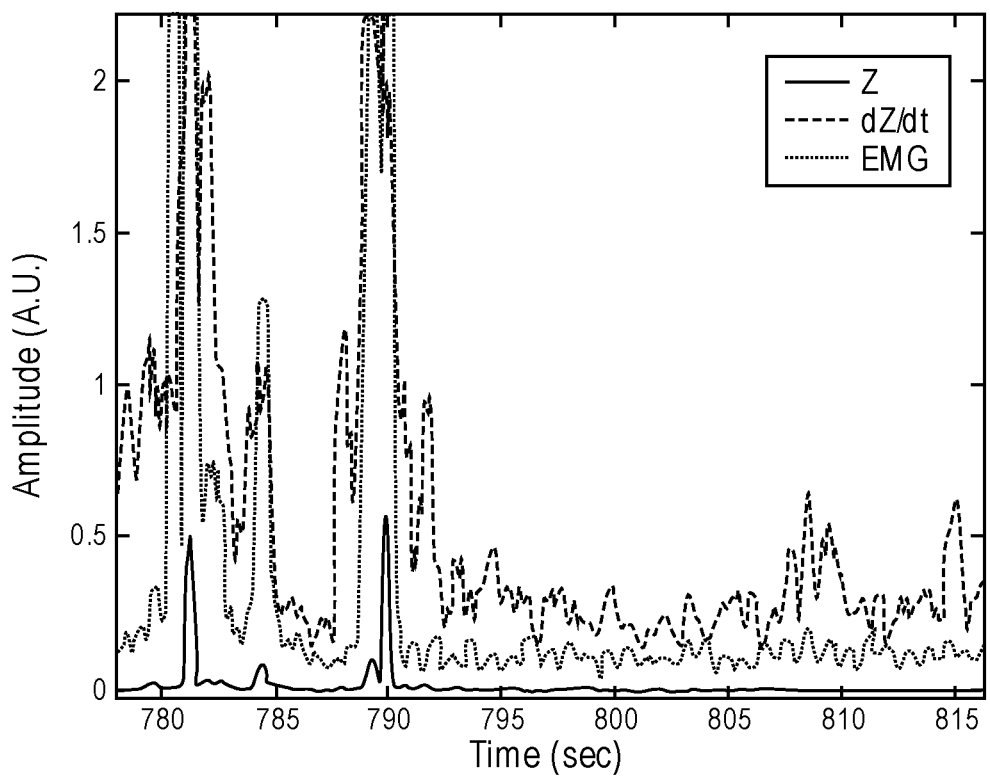
FIG. 17A shows a plot of amplitude versus time for the impedance Z measurement, a derivative dZ/dt, and a measurement of EMG voltage for a period of time of approx. 780-815 seconds after the subject has ingested cold fruit juice.
Figure 17B:
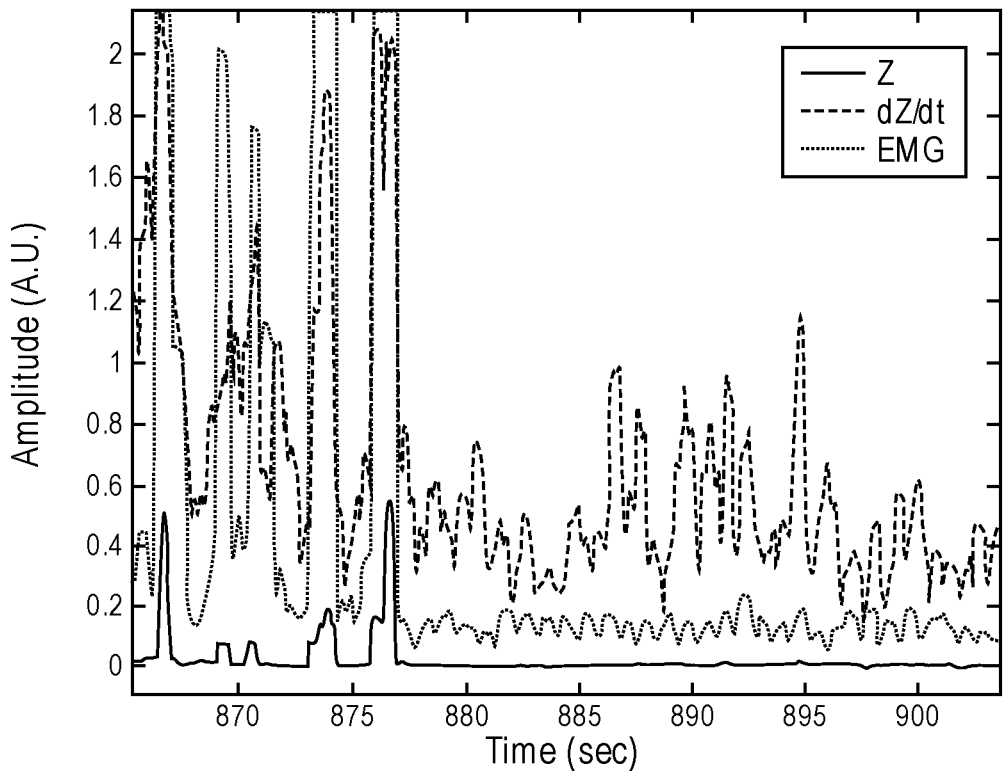
FIG. 17B shows a plot of amplitude versus time for the impedance Z measurement, a derivative dZ/dt, and a measurement of EMG voltage for a period of time of approx. 870-900 seconds after the subject has ingested cold fruit juice.
Figure 17C:
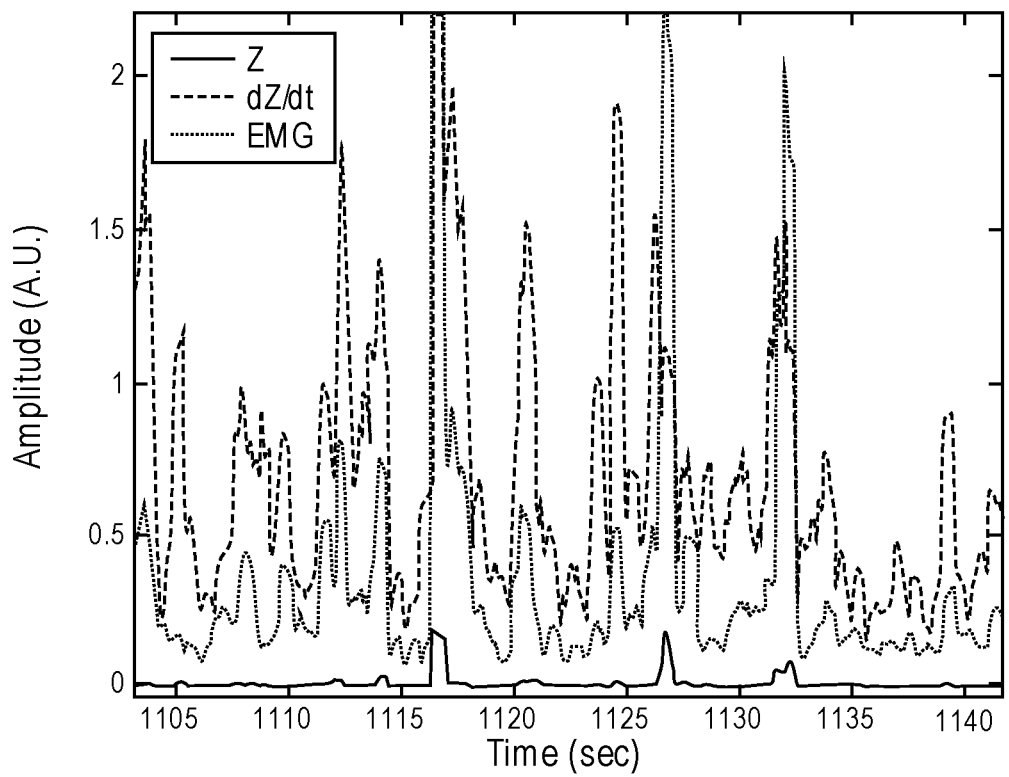
Figure 17D:
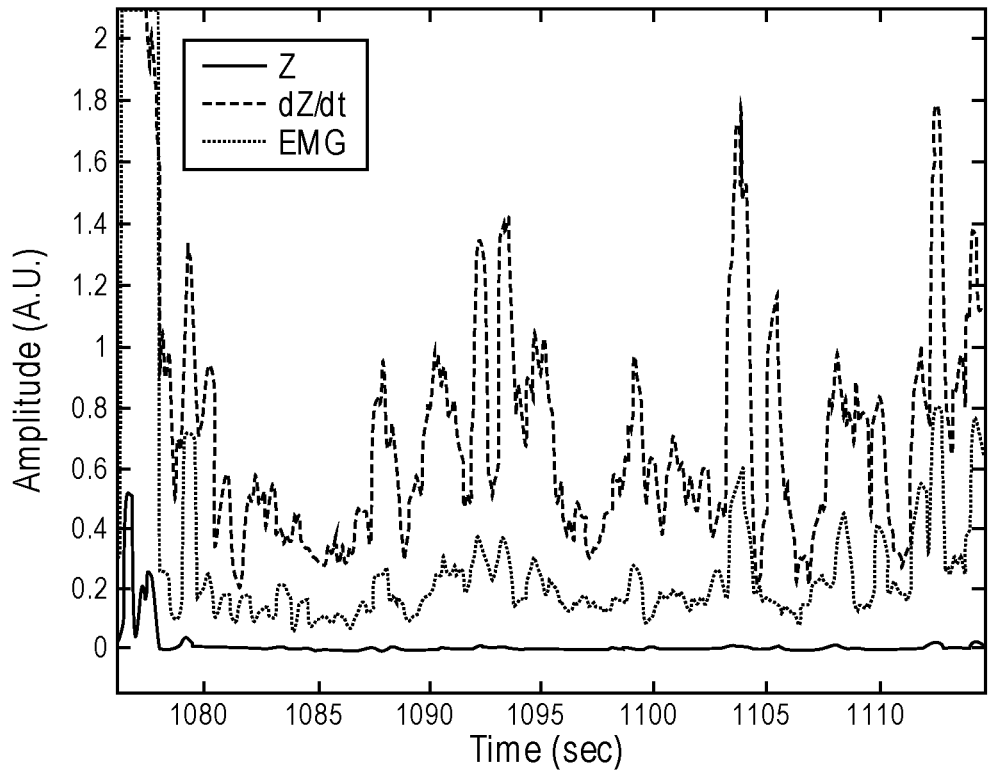

FIG. 17C shows a plot of amplitude versus time for the impedance Z measurement, a derivative dZ/dt, and a measurement of EMG voltage for a period of time of approx. 1105-1140 seconds after the subject has ingested cold fruit juice; and FIG. 17D shows a plot of amplitude versus time for the impedance Z measurement, a derivative dZ/dt, and a measurement of EMG voltage for a period of time of approx. 1080-1110 seconds after the subject has ingested cold fruit juice.

The drawing figures do not limit the current invention to the specific embodiments disclosed and described herein. The drawings are not necessarily to scale, emphasis instead being placed upon clearly illustrating the principles of the invention.

DETAILED DESCRIPTION OF PREFERRED EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

The present invention is concerned with a system for non-invasive detection and monitoring of colon activity, and specifically colon motility and contraction. The system allows for continuous or intermittent monitoring of colon motility, and can assist with behavior modification, biofeedback, post-operative care, elderly care, in-patient and outpatient care, as well as pharmacodynamic analysis. For example, the system can be used to assist with toilet training in children, non-verbal individuals, and even pets, to alert a caregiver or parent of colon activity indicative of the need to defecate or the best time to attempt toileting. The system can also be used to alert or signal caregivers of an elderly patient or nursing home resident's need for toileting, so that the caregiver can attend to the patient or resident and assist them to the restroom. The system may also alert or signal colon activity, to alert the caregiver to the need for an impending diaper change, reducing the amount of time that the patient may be soiled. The system can also be used for in-patient monitoring, such as post-operative care to provide caregivers with information regarding the patient's digestive and elimination status after surgery, and also alert caregivers when a need to toilet will arise.

This approach is applicable for both human and animal post-operative patients. The system can also facilitate monitoring of elderly or incontinent pets and help pet owners avoid "accidents" by taking the pet outside or to a litter box with it is time to defecate. The system can also be used in conjunction with pharmaceutical-based interventions for a toileting issue, such as constipation, and assist with monitoring the progress and effect of the medicament on that particular subject. The system also finds general use for analyzing the effect of a variety of medicaments on bowel function, and can assist with general pharmacodynamic analysis. In particular, the system could provide physiologic data for the delivery of precision medicine. The dose and time to maximal effect of pharmacologic agents for treatment of constipation is estimated and generalized. For a specific patient, medical providers can use data regarding bowel contractility to guide recommendations for the use of medications to assist with stooling. It will be appreciated that the system provides a distinct and important advantage over the state of the art, which requires an internally placed colonic catheter in the patient to monitor colonic motility.

Figure 1:
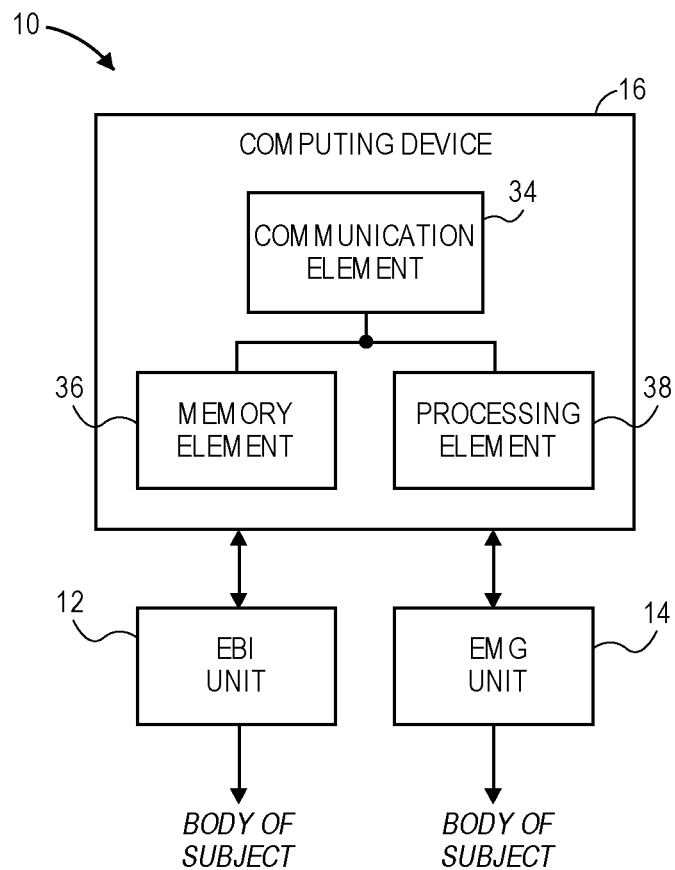
FIG. 1 is a schematic block diagram of a system, constructed in accordance with various embodiments of the current invention, for monitoring colon motility, the system comprising an electrobioimpedance (EBI) unit, an electromyography (EMG) unit, and a computing device.

The system will now be described in greater detail with reference to the drawing figures. Referring to FIG. 1, the non-invasive colon motility monitoring system 10, constructed in accordance with embodiments of the current invention, broadly comprises an electrobioimpedance (EBI) unit 12, an electromyography (EMG) unit 14, and a computing device 16.

Figure 2:
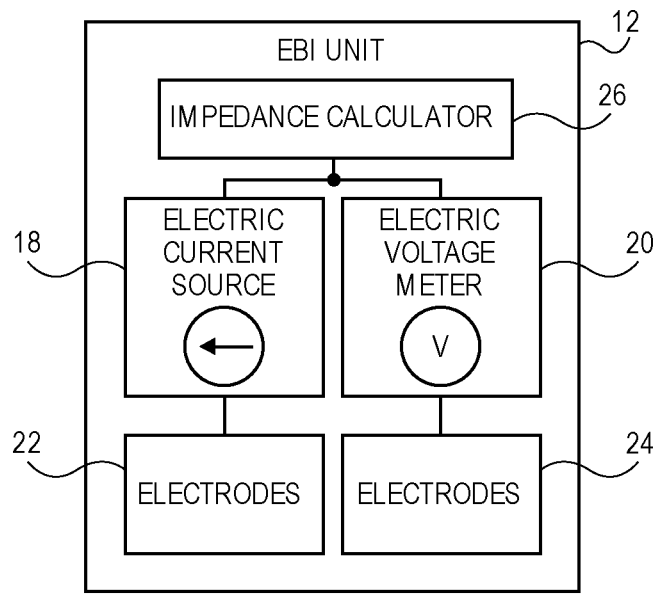
FIG. 2 is a schematic block diagram illustrating various electronic components of the EBI unit.

The EBI unit 12 generally measures an electrical impedance (Z) or electrical resistance of the body of a subject in a local region. The impedance Z measured in the colorectal region may be indicative, at least in part, of colonic activity. The EBI unit 12 includes an electric current source 18, an electric voltage meter 20, a first plurality of electrodes 22, and a second plurality of electrodes 24, as shown in FIG. 2. The EBI unit 12 may optionally include an impedance calculator 26. The electric current source 18 generates an electric current whose value is constant and/or controlled independent of the electric voltage across its terminals or the load to which it is supplying electric current. The electric current source 18 is generally configured to inject electric current into the body of the subject. The electric current source 18 includes generally known active electric/electronic circuitry which can generate constant electric current. The electric current source 18 also includes a first terminal and a second terminal. Exemplary embodiments of the electric current source 18 generate an alternating (AC) electric current with an amplitude of less than 1 milliamp (mA) and a frequency of approximately 50 kilohertz (kHz). The electric current source 18 may receive a control signal which activates it to generate the electric current.

The electric voltage meter 20 generally senses, detects, and/or measures electric voltage of an entity across its terminals. The electric voltmeter 20 includes generally known electric/electronic circuitry which senses, detects, and/or measures electric voltage. The electric voltage meter 20 also includes a first (positive) terminal and a second (negative) terminal. The electric voltage meter 20 outputs a measured voltage signal, including electric voltage levels or electric current levels that are analog or digital and/or include data, which indicates a value of the electric voltage across the terminals. The electrodes 22, 24 generally provide electrical connection to the body of the subject.

Each electrode 22, 24 includes a roughly planar contact surface formed from electrically conductive material, such as metals or metal alloys. The contact surface physically contacts the surface of the skin on the body of the subject. Each electrode 22, 24 may further include a housing which surrounds the electrically conductive contact surface and an electrically conductive wire or cable that is electrically connected to the contact surface. The wire or cable is utilized to electrically connect the electrode 22 to one of the terminals of the electric current source 18 or the electric voltage meter 20. The first electrodes 22 are associated with and coupled to or electrically connected to the electric current source 18 and may be considered or referred to as "current electrodes" 22. The second electrodes 24 are associated with and coupled to or electrically connected to the electric voltage meter 20 and may be considered or referred to as "voltage electrodes" 24.

The impedance calculator 26 generally calculates or determines the impedance Z and may include analog and/or digital circuitry, such as processors, as well as analog to digital converters (ADCs) that sample and convert analog electric voltages to digital data. In some embodiments, the electric current value generated by the electric current source 18 is known. In other embodiments, the electric current from the electric current source 18 is sensed or measured by the impedance calculator. The measured voltage signal is received from the electric voltage meter 20. In some embodiments, the electric voltage and electric current may be amplified, attenuated, level shifted, multiplied, integrated, or combinations thereof by the impedance calculator to output a measured impedance signal that varies according to, corresponds to, or includes a value of the measured impedance Z. In other embodiments, the electric voltage and/or electric current may be sampled and converted to digital voltage and current values, respectively, by ADCs. If the value of the electric current is already known, then the digital voltage values may be divided by a constant value representing the electric current. Otherwise, the digital voltage values may be divided by the digital current values. Either way, the impedance calculator 26 outputs the measured impedance signal including a stream, series, or sequence of sampled values in digital data format indicating the value of the impedance Z. Furthermore, electric current may be injected by the electric current source 18 in a plurality of locations and electric voltage may be measured by the electric voltage meter 20 in the same locations. The impedance calculator 26 may determine or calculate an average of the electric current values and the electric voltage values to determine or calculate an average impedance Z. The measured impedance signal may vary according to, correspond to, or include an average value of the measured impedance Z.

Figure 3A:
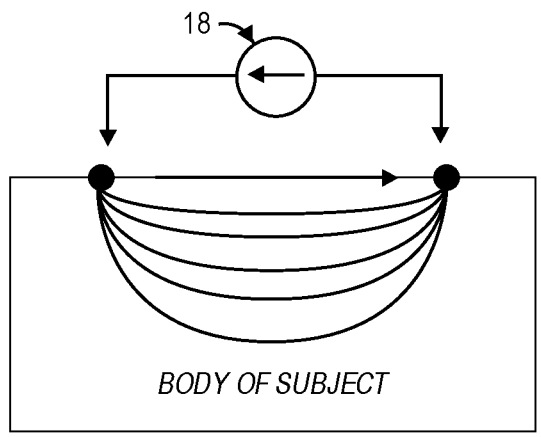
FIG. 3A is a schematic block diagram illustrating injection of electric current into a body of a subject.
Figure 3B:
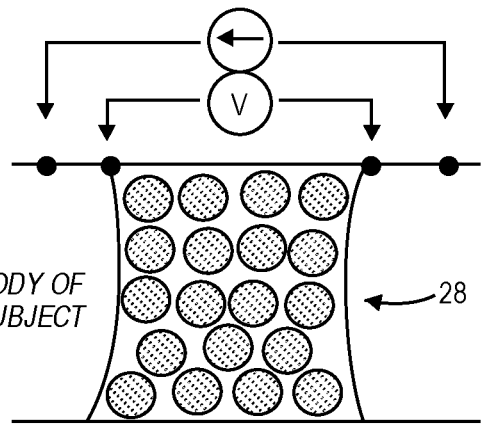
FIG. 3B is a schematic block diagram illustrating injection of electric current into the body of a subject and measurement of electric voltage at the site of injection of electric current.

The EBI unit 12 operates as follows. The EBI unit 12 may receive a control signal which is also received by the electric current source 18. Upon receipt of the control signal, the electric current source 18 generates electric current which is injected into the body of the subject as indicated by the arrows in FIG. 3A. The electric current flows through the body of the subject, as indicated by the curved lines in FIG. 3A. The electric current source 18 may generate electric current for as long as the control signal is received or for a predetermined period of time after the control signal is received. In general, electric current flowing though the body of the subject creates an electric field 28, as shown in FIG. 3B. The electric voltage meter 20 measures the voltage of the electric field 28 as indicated by the arrows in FIG. 3B. As a general rule, the electric voltage is measured between the points where the electric current is injected. If the EBI unit 12 includes the impedance calculator 26, then the impedance calculator 26 receives the measured voltage signal from the electric voltage meter 20 and, optionally, the electric current signal from the electric current source 18. The impedance calculator 26 outputs the measured impedance signal, which is also output by the EBI unit 12. Typically, the measured impedance signal includes a stream, series, or sequence of sampled values in digital data format of the impedance Z. In other embodiments, the EBI unit 12 may output the measured voltage signal and, optionally, the electric current signal.

Figure 4:
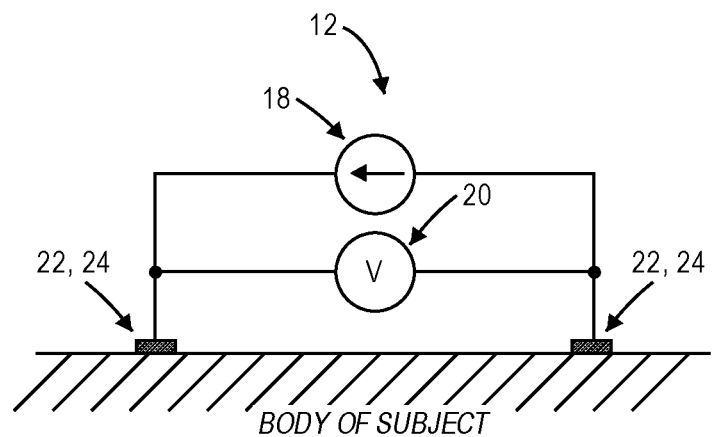
FIG. 4 is a schematic block diagram illustrating a first configuration of electrodes used with the EBI unit.
Figure 5:
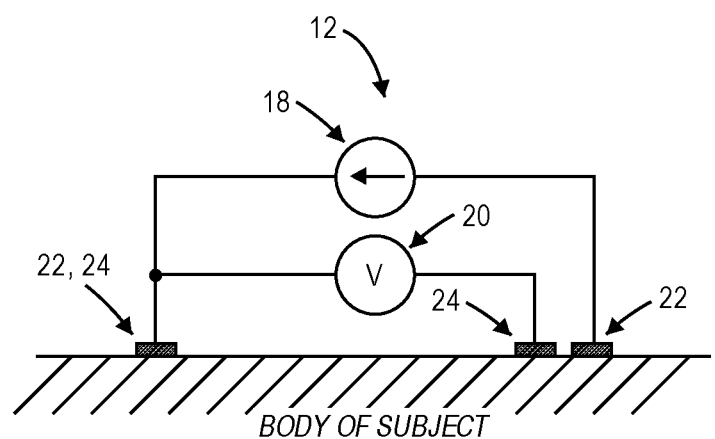
FIG. 5 is a schematic block diagram illustrating a second configuration of electrodes used with the EBI unit.
Figure 6:
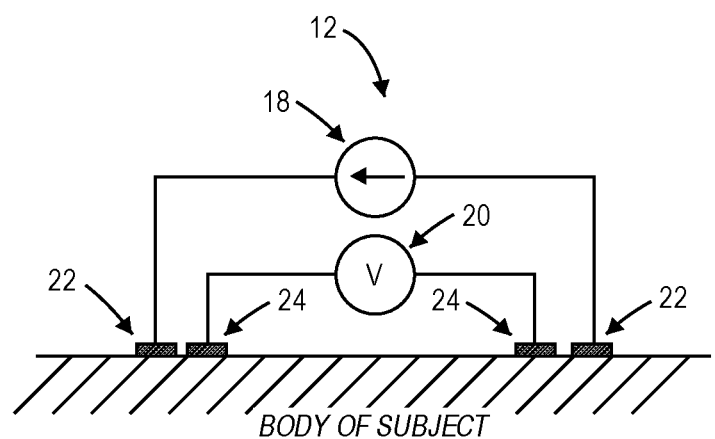
FIG. 6 is a schematic block diagram illustrating a third configuration of electrodes used with the EBI unit.
Figure 10:
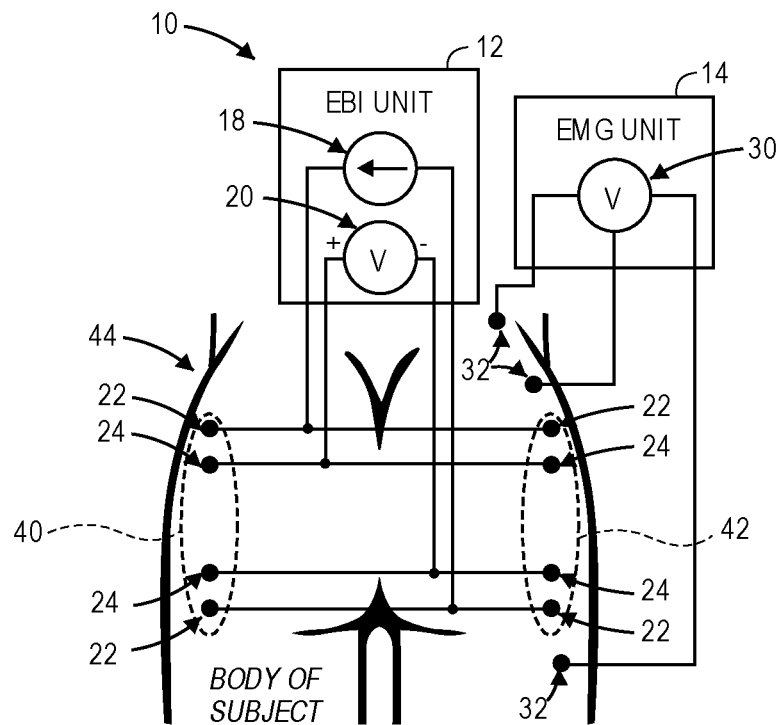
FIG. 10 is a schematic block diagram illustrating a placement, with relation to the body of the subject, of electrodes connected to the EBI unit and electrodes connected to the EMG unit.

If electric current is injected in a plurality of locations and electric voltage is measured in those locations, then the measured impedance signal may vary according to, correspond to, or include an average value of the measured impedance Z for the region bounded by the locations of electric current injection and electric voltage measurement. In exemplary embodiments, the EBI unit 12 includes eight electrodes 22, 24, coupled to or electrically connected to the electric current source 18 and the electric voltage source 18 as shown in FIG. 10, with four current electrodes 22 and four voltage electrodes 24. The impedance calculator 26 receives the measured electric voltages and is provided with the electric current values. The impedance calculator 26, and hence, the EBI unit 12, outputs the measured impedance signal which includes a stream, series, or sequence of sampled values in digital data format of the average impedance Z of the region of the body of the subject that is bounded by the eight electrodes 22, 24. Furthermore, when positioning or placing the electrodes 22, 24 for impedance measurement, two current electrodes 22 are positioned spaced apart from one another and two voltage electrodes 24 are positioned spaced apart from one another and in between the two current electrodes 22. In alternative configurations, the EBI unit 12 may include two, three, or four electrodes 22, 24 as shown in FIGS. 4, 5, and 6, respectively. The electrodes 22, 24 may be electrically connected to the electric current source 18 and the electric voltage source 18 as shown in the figures.

Figure 7:
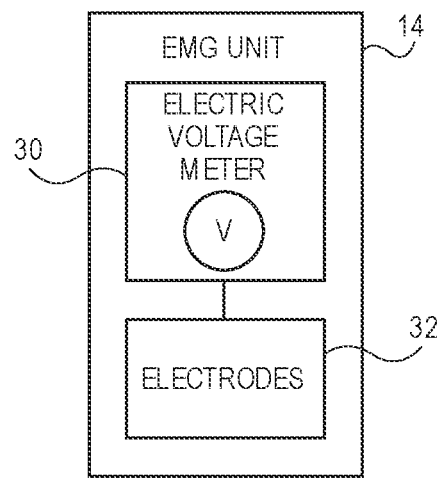
FIG. 7 is a schematic block diagram illustrating various electronic components of the EMG unit.

The EMG unit 14 generally measures an (EMG) electric voltage of the body of a subject in a local region. The EMG voltage is indicative of skeletal muscle activity in the region where it is measured. The EMG unit 14 includes an electric voltage meter 30 and a third plurality of electrodes 32, as shown in FIG. 7, and considered or referred to as "EMG electrodes" 32. The electric voltage meter 30 may include three terminals—two of which may be considered the main terminals, while the third terminal may be considered a reference terminal. The electric voltage meter 30 may include electric/electronic circuitry which senses, detects, and/or measures electric voltage between any two of the three terminals.

Figure 8:
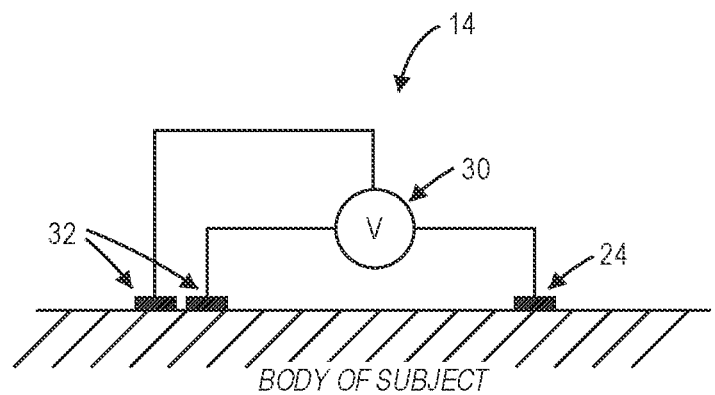
FIG. 8 is a schematic block diagram illustrating a configuration of electrodes used with the EMG unit.
Figure 9A:
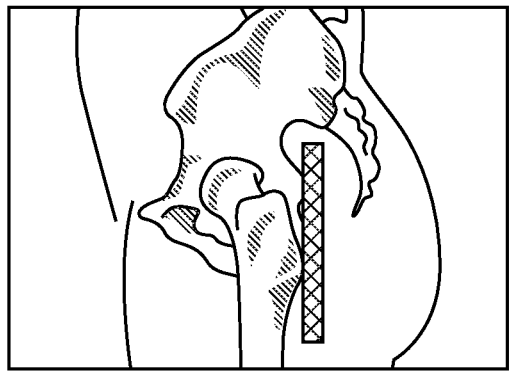
FIG. 9A is a view of a human body indicating a location by a hatched box of recommended electrode placement for measuring an impedance Z in relation to the skeletal structure.
Figure 9B:
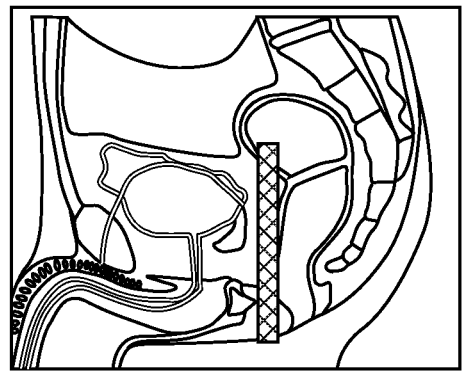
FIG. 9B is a view of a human body indicating a location by a hatched box of recommended electrode placement for measuring an impedance Z in relation to the colon position.
Figure 9C:
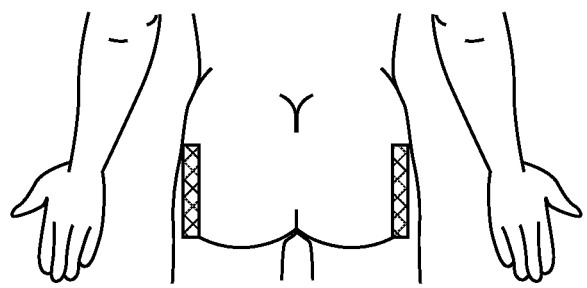
FIG. 9C is a view of a human body indicating a location by a hatched box of recommended electrode placement for measuring an impedance Z in relation to the posterior external view of subject.
Figure 9D:
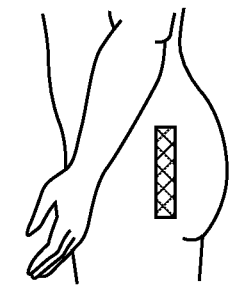
FIG. 9D is a view of a human body indicating a location by a hatched box of recommended electrode placement for measuring an impedance Z in relation to the side external view of subject.

Each EMG electrode 32 is substantially identical in structure, function, and operation to one of the electrodes 22, 24. Each EMG electrode 32 is coupled to or electrically connected to one of the terminals of the electric voltage meter 30. The EMG electrodes 32 are connected to the body of the subject as shown in FIG. 8. The EMG unit 14 outputs an EMG voltage signal including electric voltage levels or electric current levels that are analog or digital and/or include data, which varies according to, corresponds to, or indicates a value of the measured electric voltage across two of the three terminals. Typically, the EMG voltage signal includes a stream, series, or sequence of sampled values in digital data format of the electric voltage across two of the three terminals and, in turn, the electric voltage across two of the three EMG electrodes 32, which is the EMG voltage.

The computing device 16 generally performs processing, calculations, computations, etc. to monitor colon activity. The computing device 16 includes a communication element 34, a memory element 36, and a processing element 38, as shown in FIG. 1. The computing device 16 may further include components such as a graphic display or a touchscreen, a keypad, a keyboard, a mouse, audio speakers, and other user interface devices that are well known and will not be discussed in detail.

The communication element 34 generally allows the computing device 16 to communicate with other computing devices, external systems, networks, and the like. The communication element 34 may include signal and/or data transmitting and receiving circuits, such as antennas, amplifiers, filters, mixers, oscillators, digital signal processors (DSPs), and the like. The communication element 34 may establish communication wirelessly by utilizing radio frequency (RF) signals and/or data that comply with communication standards such as cellular 2G, 3G, 4G, Voice over Internet Protocol (VoIP), LTE, Voice over LTE (VoLTE) or 5G, Institute of Electrical and Electronics Engineers (IEEE) 802.11 standard such as WiFi, IEEE 802.16 standard such as WiMAX, Bluetooth™, or combinations thereof. In addition, the communication element 34 may utilize communication standards such as ANT, ANT+, Bluetooth™ low energy (BLE), the industrial, scientific, and medical (ISM) band at 2.4 gigahertz (GHz), or the like. Thus, the communication element 34 may include wireless transceivers configured to wirelessly transmit and receive data through one of these communications standards between the computing device and the EBI unit 12 and/or EMG unit 14. The communication element 34 may include a single transceiver to wirelessly communicate the control signal, the measured impedance signal, and the EMG voltage signal to and from the computing device 16, or the communication element 34 may include one transceiver for each of the listed signals.

Alternatively, or in addition, the communication element 34 may establish communication through connectors or couplers that receive metal conductor wires or cables which are compatible with networking technologies such as Ethernet. In certain embodiments, the communication element 34 may also couple with optical fiber cables. The communication element 34 may be in electronic communication with the memory element 36 and the processing element 38.

The memory element 36 may be embodied by devices or components that store data in general, and digital or binary data in particular, and may include exemplary electronic hardware data storage devices or components such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element 36 may be embedded in, or packaged in the same package as, the processing element 38. The memory element 36 may include, or may constitute, a "computer-readable medium". The memory element 36 may store the instructions, code, code statements, code segments, software, firmware, programs, applications, apps, services, daemons, or the like that are executed by the processing element 38. The memory element 36 may also store settings, data, documents, sound files, photographs, movies, images, databases, and the like.

The processing element 38 may comprise one or more processors. The processing element 38 may include electronic hardware components such as microprocessors (single-core or multi-core), microcontrollers, digital signal processors (DSPs), field-programmable gate arrays (FPGAs), analog and/or digital application-specific integrated circuits (ASICs), or the like, or combinations thereof. The processing element 38 may generally execute, process, or run instructions, code, code segments, code statements, software, firmware, programs, applications, apps, processes, services, daemons, or the like. The processing element 38 may also include hardware components such as registers, finite-state machines, sequential and combinational logic, and other electronic circuits that can perform the functions necessary for the operation of the current invention. In certain embodiments, the processing element 38 may include multiple computational components and functional blocks that are packaged separately but function as a single unit. In some embodiments, the processing element 38 may include ADCs that sample and convert analog electric voltages to digital data. The processing element 38 may be in electronic communication with the other electronic components through serial or parallel links that include universal busses, address busses, data busses, control lines, and the like.

The processing element 38 may be operable, configured, or programmed to perform the following functions by utilizing hardware, software, firmware, or combinations thereof. The processing element 38 generates the control signal and communicates it to the electric current source 18 of the EBI unit 12. The control signal may be a pulse of electric voltage or electric current that initiates the impedance measurement, or the control signal may be a constant value of electric voltage or electric current that is transmitted for a time period during which impedance is measured. The processing element 38 receives the EMG voltage signal from the EMG unit 14. Typically, the EMG voltage signal is a stream of digital data sampled values of the electric voltage across two of the three EMG electrodes 32. Alternatively, the EMG voltage signal may include analog voltage levels that correspond to the measured EMG voltage. The ADCs of the processing element 38 may convert the EMG voltage signal into a stream of digital data sampled values.

The processing element 38 receives the measured impedance signal from the EBI unit 12. Typically, the measured impedance signal is a stream of digital data sampled values of the impedance Z. Alternatively, the processing element 38 may receive the measured voltage signal from the electric voltage meter 20 of the EBI unit 12. If the electric current from the electric current source 18 is known, then the processing element 38 calculates the impedance Z as the digital data sampled values of measured voltage divided by the electric current value.

The processing element 38 calculates, computes, or determines a derivative, dZ/dt, of the impedance Z values utilizing known derivative or slope calculation techniques. Since the impedance Z is a stream of digital data samples, the derivative dZ/dt is also a stream of digital data values. Given values of the EMG voltage, the impedance Z, and the derivative dZ/dt, the processing element 38 calculates, computes, or determines a first correlation between the EMG voltage and the impedance Z, a second correlation between the EMG voltage and the derivative dZ/dt, and a third correlation between the impedance Z and the derivative dZ/dt. In certain embodiments, one or more of the data streams of the EMG voltage, the impedance Z, or the derivative dZ/dt are conditioned, such as by filtering, averaging, and/or applying variability analysis, before calculating, computing, or determining the first, second, and third correlations.

The processing element 38 may store the stream of values of the EMG voltage, the impedance Z, and the derivative dZ/dt, as well as the first correlation, the second correlation, and the third correlation in the memory element 36. The processing element 38 may also display values of the EMG voltage, the impedance Z, and the derivative dZ/dt and/or statistics of the values (e.g., averages, standard deviations, high values, low values, etc.) on a display or screen. In addition, or instead, processing element 38 may display values of the EMG voltage, the impedance Z, and the derivative dZ/dt as waveforms of values versus time.

In general, changes in the impedance Z without significant changes in EMG voltage are indicative of colon activity. The EMG voltage measurement may act to filter out noise and isolate the measurement of the impedance Z. The filtering may help to distinguish between physical movement of the subject's body, such as arm and/or leg movement, and internal organ—specifically the colon—activity.

The processing element 38 utilizes one or more of the first, second, and/or third correlations to monitor colon activity and to determine, detect, or predict that a bowel event, such as a bowel movement, is about to occur. In particular, the processing element 38 may determine when at least one of the correlations has a value above or below a predetermined threshold value or when at least one of the correlations has a value within a predetermined range of values. In addition, or instead, the processing element 38 may determine when one of the correlations has a value within a predetermined first range of values and another of the correlations has a value within a predetermined second range of values. In a first exemplary embodiment, the processing element 38 may determine that a bowel event is about to occur when the first correlation (between the EMG voltage and the impedance Z) has a value greater than 0.75. In a second exemplary embodiment, the processing element 38 may determine that a bowel event is about to occur when the first correlation (between the EMG voltage and the impedance Z) is relatively high, i.e., has a value greater than 0.75, and the third correlation (between the impedance Z and the derivative dZ/dt) is relatively low, i.e., has a value between approximately 0 and approximately 0.25.

When the processing element 38 determines that a bowel event is about to occur, it may provide an indication of the event by performing one or more of the following: activate a (warning) light, play a sound (such as an alarm or an alert) through a speaker, vibrate a device, display a message on a screen, send a text message, send an email message, send an automated audio message, play a ringtone, activate a smart phone app notification, activate a smart wearable electronic device, such as a watch or glasses, activate an implanted electronic device, etc.

The system 10 may also have a learning, or profile development, mode in which the processing element 38 collects a volume of data of the impedance Z values and the EMG voltage values for a particular subject or individual. Typically, the learning mode occurs in known or controlled conditions so that data can be captured when the subject is resting for normal (no bowel event impending) circumstances and bowel event circumstances. The processing element 38 may utilize artificial intelligence, algorithms, statistical models, or the like, or combinations thereof to determine baseline values or levels of impedance Z data and EMG voltage data. Additionally, or alternatively, the baseline values or levels of impedance Z data and EMG voltage data may be manually input or indicated. After the baseline values or levels have been established, the processing element 38 may operate in a normal mode as described above.

The system 10 may operate or function as follows. The electrodes 22, 24 for the EBI unit 12 are placed for contact with the skin of the body of the subject as shown in FIG. 10. Using this configuration creates an electrical field circulating between two pairs of electrodes 22 from the electric current source 18 arranged in a quadrilateral configuration on the posterior side of the subject in the gluteal region so that the electrical field is centered over the colon region, and two pairs of electrodes 24 from the electric voltage meter 20 arranged with one pair of voltage electrodes 24 proximate to each pair of current electrodes 22 and within the electrical field created thereby.

Referring to FIGS. 9 and 10, in order to center the electrical field over the colon, the current electrodes 22 are preferably positioned such that two electrodes 22 are positioned on each posterior side of the body, and aligned substantially along a plane, as indicated by the hatched boxes in FIGS. 9A-9D, defined by the mid axillary line of the thorax, such that the front-to-back alignment of the electrodes 22 in a lateral (side) view of the pelvis is generally between the ischial spine and coccyx. The superior-inferior (top-to-bottom) alignment of the electrodes 22 from the electric current source 18 is such that a (superior) pair of electrodes 22 is coupled in a spaced apart relationship with one electrode 22 on each side of the body below the iliac crest, and preferably below a plane in general horizontal alignment with the posterior superior iliac spine. The second (inferior) pair of electrodes 22 is coupled in a spaced apart relationship on each side of the body along a plane in general horizontal alignment with the rectum, and vertically aligned with the other respective electrode 22 on that side of the body. As such, in a posterior view of the body, the four current generating electrodes may be characterized as defining a quadrilateral perimeter "framing" the gluteal region. As illustrated in FIGS. 9A-9D, such positioning allows the generated electrical field to avoid "interference" from the tail bone, femur, hip and other bones in the region of interest, so that impedance Z measurements will be based upon internal colonic motility. The voltage electrodes 24 are positioned interior to the quadrilateral perimeter so as to detect the initial electrical current and changes thereto. Preferably, a first pair of voltage electrodes 24 are positioned with one each proximate to, but below each of the superior current electrodes 22, and a second pair of voltage electrodes 24 proximate to, but above each of the inferior current electrodes 22, as illustrated in FIG. 10. More preferably, the respective current electrodes 22 and the voltage electrodes 24 on each side of the body are in general vertical alignment. Thus, it will be appreciated that the superior and inferior current electrodes 22 (i.e., "outer" electrodes of the configuration) continuously send and receive electrical signal to apply very low constant alternating current, while the voltage electrodes 24 (i.e., "inner" electrodes) intermittently or constantly detect and measure impedance and receive the applied electric current. Expressed in another way, the current electrodes 22 and the voltage electrodes 24 that are configured to contact the left side of the body of the subject form a first impedance measurement group 40, while the current electrodes 22 and the voltage electrodes 24 that are configured to contact the right side of the body of the subject form a second impedance measurement group 42.

The EMG electrodes 32 are placed for contact with the skin of the body of the subject as shown in FIG. 10. Two of the EMG electrodes 32 are positioned in general vertical alignment with the electrodes 22, 24 of either the first impedance measurement group 40 or the second impedance measurement group 42 on one side of the body. In the exemplary embodiment shown in FIG. 10, the EMG electrodes 32 are positioned in general vertical alignment with the electrodes 22, 24 of the second impedance measurement group 42 on the right side of the body. One of the EMG electrodes 32 is preferably positioned superior to the superior current electrode 22, closer to the horizontal plane defined by the iliac crest, while the other EMG electrode 32 is preferably positioned inferior to the inferior current electrode 22, such as on the upper lateral portion of the thigh, as illustrated in FIG. 10. A third EMG electrode 32 is preferably positioned in the vicinity of the other EMG electrodes 32 near the waist to act as the reference signal.

The electrodes 22, 24, 32, when positioned in the relative locations as described above, form an array 44 of electrodes 22, 24, 32 for monitoring colon motility. The array 44 includes eleven electrodes 22, 24, 32 in total with eight electrodes 22, 24 associated with measuring impedance Z and configured to electrically connect to the EBI unit 12 and three electrodes 32 associated with measuring EMG voltage and configured to electrically connect to the EMG unit 14. Four current electrodes 22 provide electric current injection (from the electric current source 18) with each current electrode 22 positioned in a successive one of the four corners of a first quadrilateral. Four voltage electrodes 24 provide electric voltage measurement (from the electric voltage meter 20) with each voltage electrode 22 positioned in a successive one of the four corners of a second quadrilateral, wherein the second quadrilateral is smaller in one dimension than the first quadrilateral and is positioned generally within the first quadrilateral. A first pair of the voltage electrodes 24 are generally aligned with a first pair of the current electrodes 22 and form the first impedance measurement group 40. A second pair of the voltage electrodes 24 are generally aligned with a second pair of the current electrodes 22 and form the second impedance measurement group 42. Two of the EMG electrodes 32 are positioned in general alignment with either the first impedance measurement group 40 or the second impedance measurement group 42 with one EMG electrode 32 positioned adjacent one end of the group 40, 42 and the other EMG electrode 32 positioned at the other end of the group 40, 42. The third EMG electrode 32 is positioned in the vicinity of the first two EMG electrodes 32 an generally outside of the bounds of the first quadrilateral.

When all electrodes 22, 24, 32 have been placed, the processing element 38 may initiate impedance Z measurement and EMG measurement by communicating a control signal to at least the EBI unit 12. In certain embodiments, the EBI unit 12 and the EMG unit 14 may operate automatically. In any case, the EBI unit 12 communicates the measured impedance signal to the processing element 38 of the computing device 16 so that the processing element 38 receives the stream of digital data sampled values of the impedance Z. In addition, the EMG unit 14 communicates the EMG voltage signal to the processing element 38 of the computing device 16 so that the processing element 38 receives the stream of digital data sampled values of the EMG voltage.

The system 10 may be manually or automatically placed in the learning mode, in which the processing element 38 determines baseline values or levels of impedance Z data and EMG voltage data for a particular subject or individual. After the learning mode is complete, or if the learning mode is not utilized, the processing element 38 calculates, computes, or determines the derivative $dZ/dt$ of the impedance Z values. The processing element 38 also calculates, computes, or determines the first correlation, the second correlation, and the third correlation. The processing element 38 utilizes one or more of the first, second, and/or third correlations to determine, detect, or predict that a bowel event is about to occur. Generally, the processing element 38 determines that a bowel event is about to occur when one or more of the correlations has a value within a predetermined range of values. When the processing element 38 determines that a bowel event is about to occur, it may provide an indication of the event such as by activating a light, sounding an alarm, or sending a notification.

Figure 11:
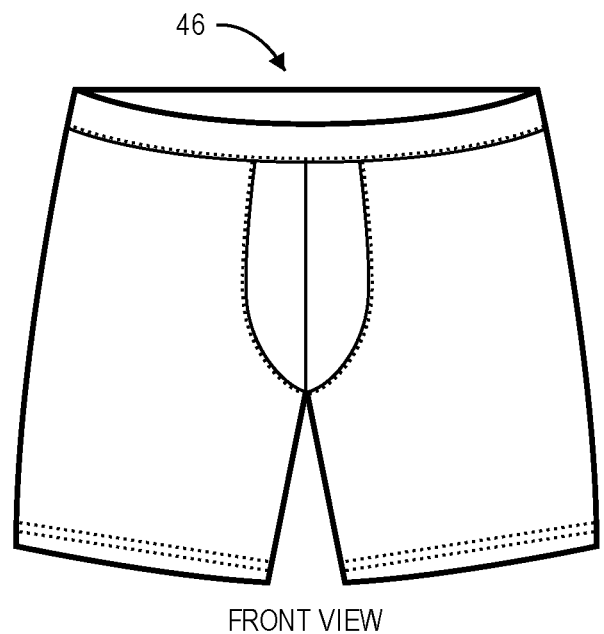
FIG. 11 is a front view of an article of clothing utilized in various embodiments of the current invention.
Figure 12:
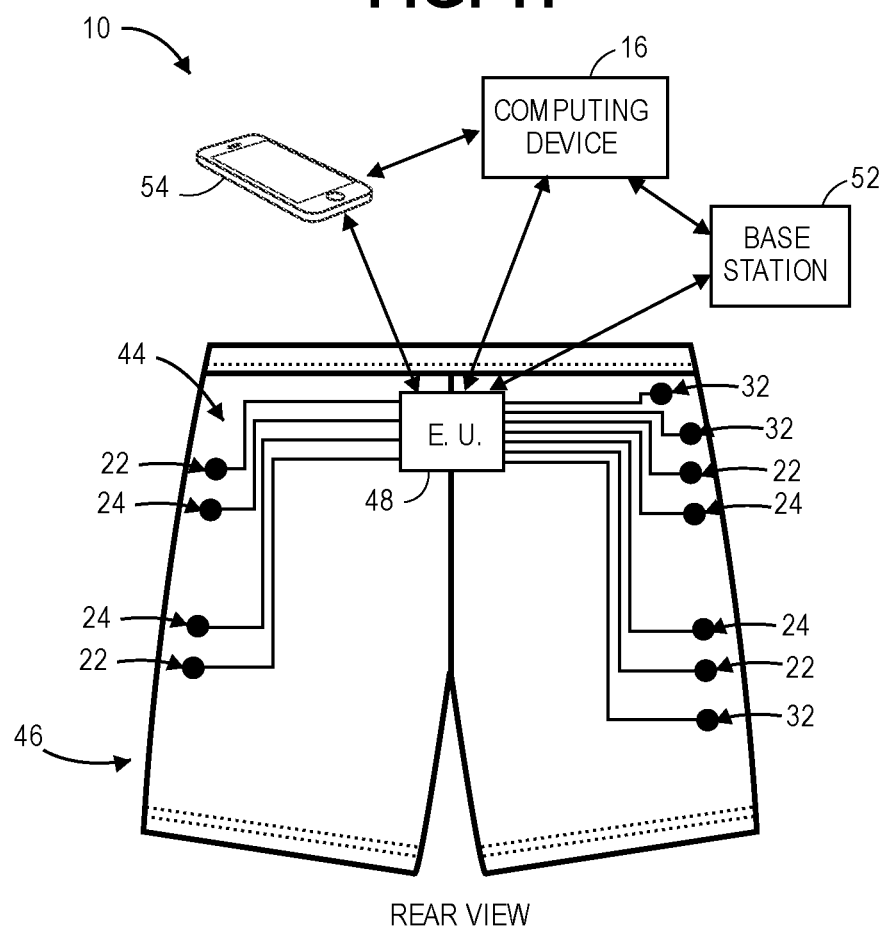
FIG. 12 is a rear view of the article of clothing in FIG. 11 further illustrating an electronics unit and the placement of electrodes for the EBI unit and electrodes for the EMG unit.
Figure 13:
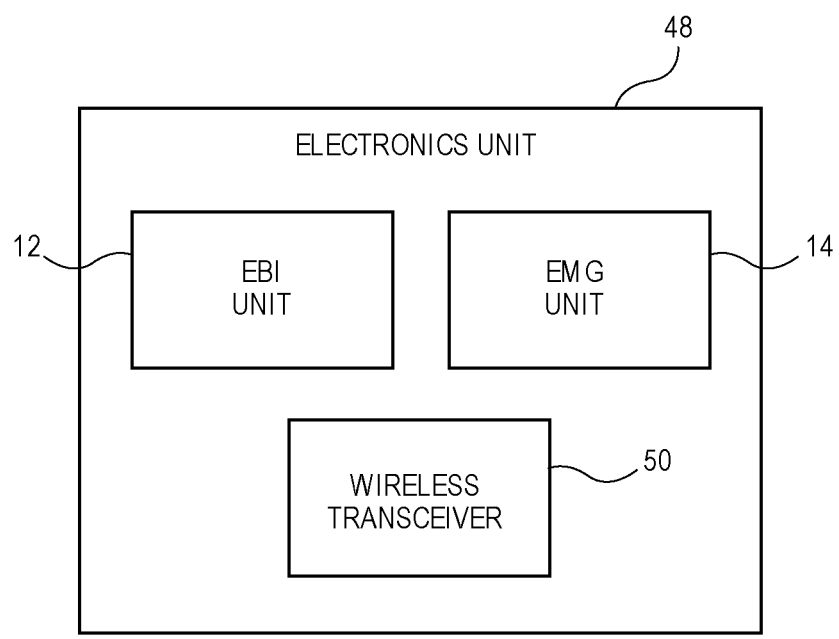
FIG. 13 is a schematic block diagram illustrating various electronic components of the electronics unit.
Figure 14A:
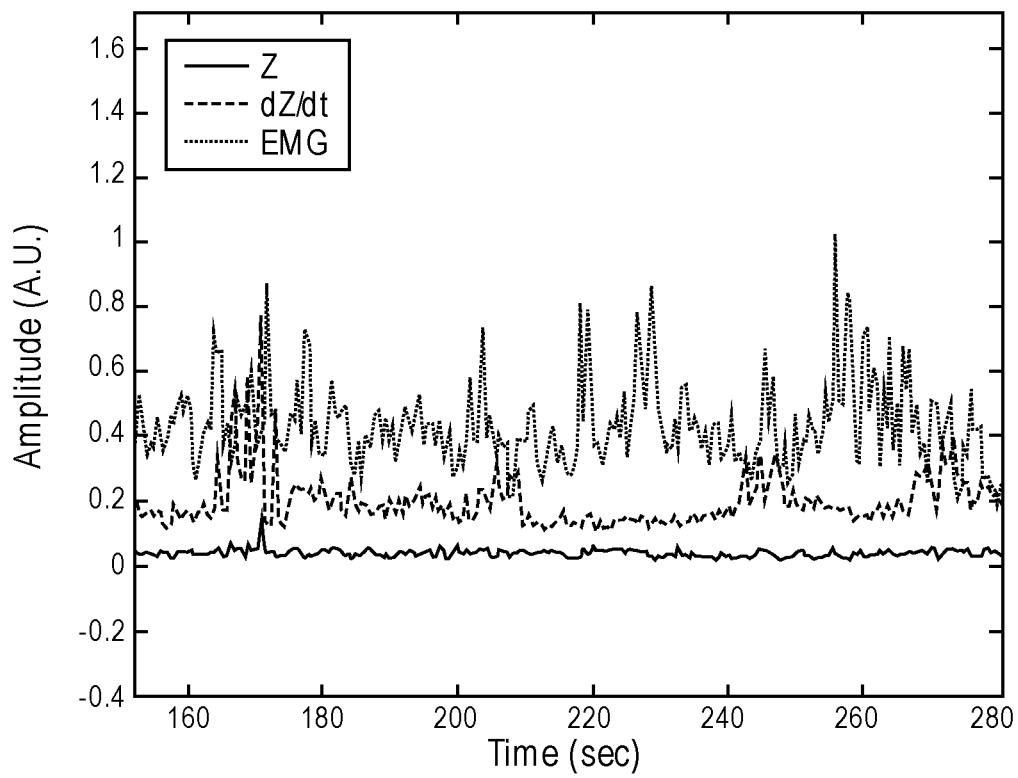
FIG. 14A shows a plot of amplitude versus time for the impedance Z measurement, a derivative dZ/dt, and a measurement of EMG voltage for various clinical situations for each step of the protocol with the subject resting in a semi-recumbent position.
Figure 14B:
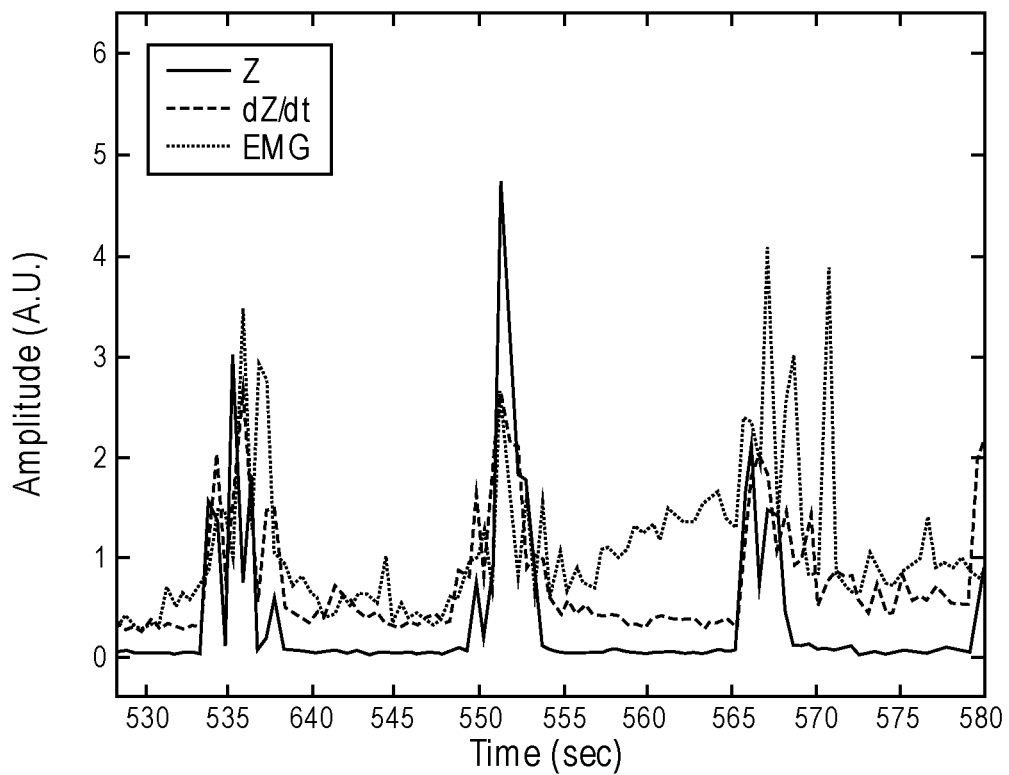
FIG. 14B shows a plot of amplitude versus time for the impedance Z measurement, a derivative dZ/dt, and a measurement of EMG voltage with the induced disturbance of leg lifting.
Figure 14C:
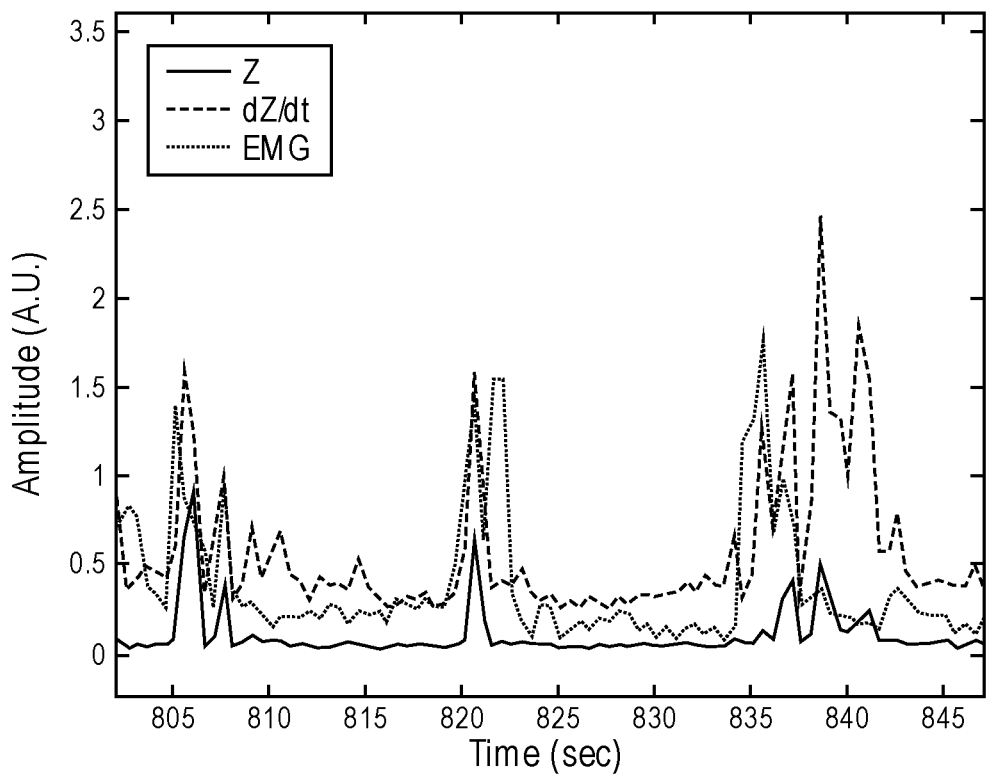
FIG. 14C shows a plot of amplitude versus time for the impedance Z measurement, a derivative dZ/dt, and a measurement of EMG voltage with the induced disturbance of stomach pressing.
Figure 14D:
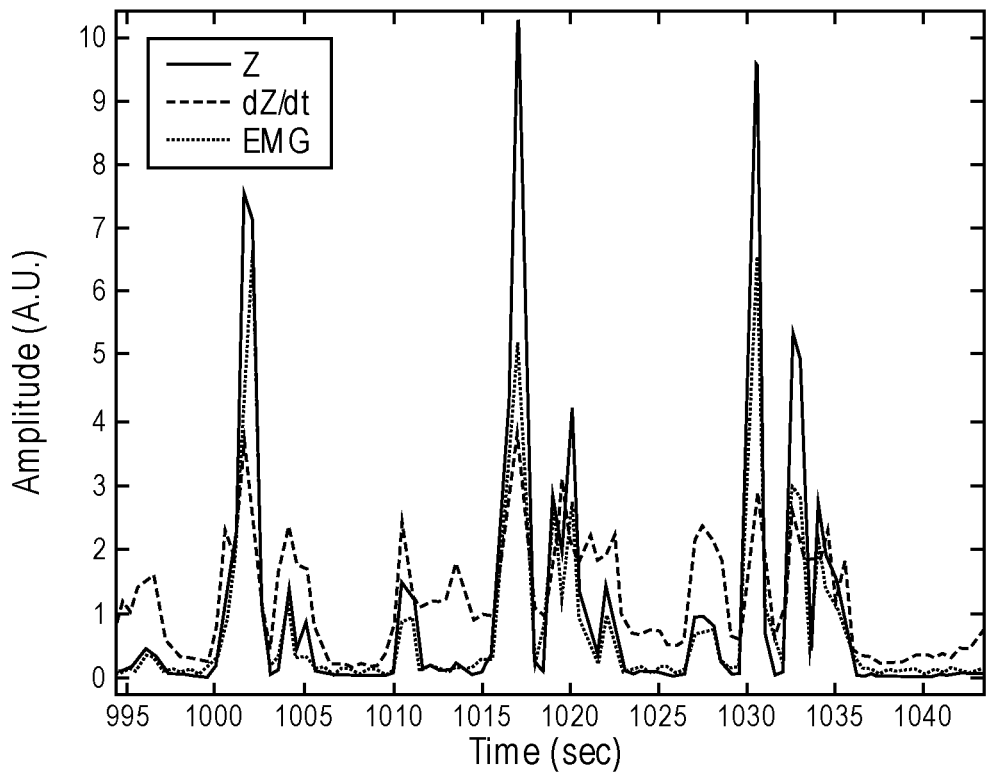
FIG. 14D shows a plot of amplitude versus time for the impedance Z measurement, a derivative dZ/dt, and a measurement of EMG voltage with the induced disturbance of internal pushing (bearing down)
Figure 14E:
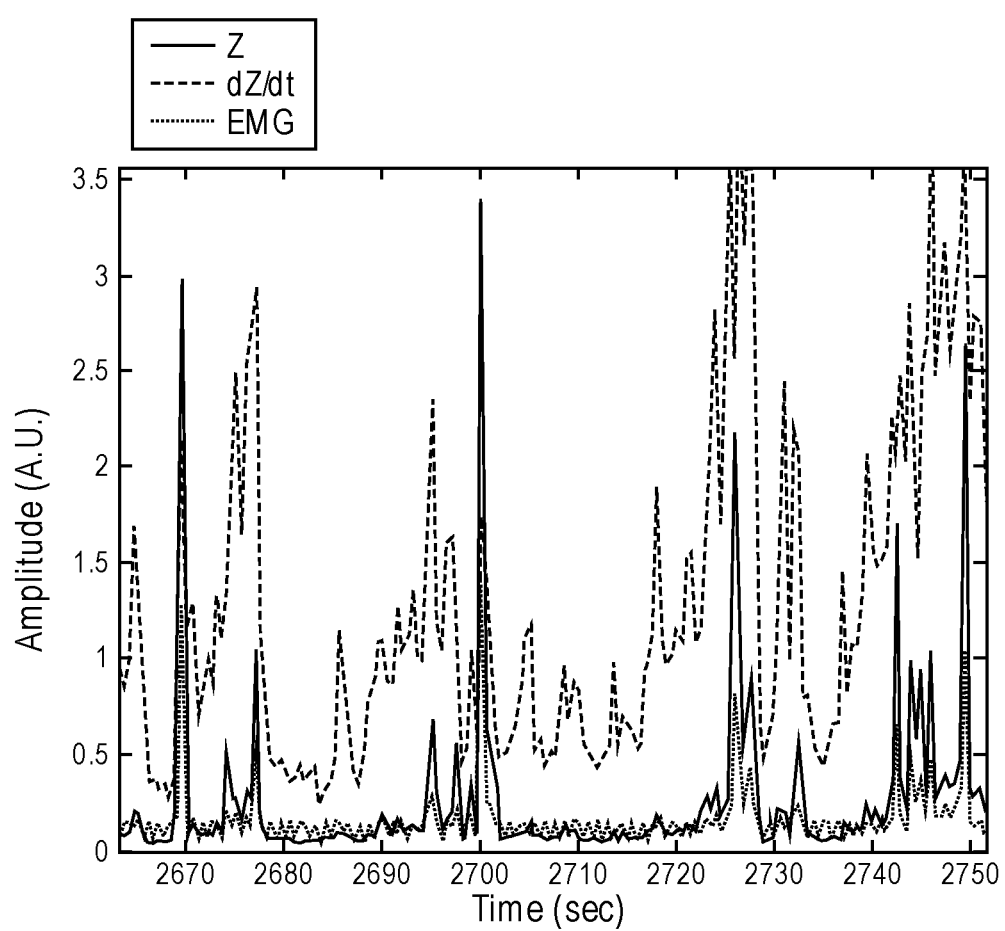
FIG. 14E shows a plot of amplitude versus time for the impedance Z measurement, a derivative dZ/dt, and a measurement of EMG voltage with the induced disturbance of medication (laxative)

Referring to FIGS. 11-13, various embodiments of the system 10 may include an article of clothing 46 that retains at least the EBI unit 12 and the EMG unit 14 included in an electronics unit 48. The article of clothing 46 may be any suitable garment or apparel configured for wearing by the subject in proximity to the colorectal region of the subject and in contact with the skin of the patient, such as underwear, a cloth or disposable-type diaper, training pants, a girdle, pants, panty hose, shorts, briefs, boxer-briefs, and the like. It will be appreciated that in order to correctly position the components of the system 10, the article of clothing 46 or certain regions of the article of clothing 46 will generally be close-fitting to the body of the subject (aka "skintight"), as opposed to a loose garment, and may be embodied by underwear or undershorts that are gender-specific or unisex. The electrodes 22, 24, 32 are retained by, or coupled to, the body of the article of clothing 46 such as being embedded into the fabric, such that the contact surface of each electrode 22, 24, 32 contacts the skin of the body of the subject when the article of clothing 46 is worn in a normal fashion. Each electrode 22, 24, 32 is positioned within the article of clothing 46 to contact the subject's skin in the same location as described above and shown in FIG. 10 or as are described for the array 44 of electrodes 22, 24, 32. The electronics unit 48 may additionally include an electric power source, such as a battery, and packaging that allows the electronics unit 48 to comfortably be accommodated when the article of clothing 46 is worn in a normal fashion.

In some embodiments, a (single conductor or multi conductor) cable may electrically connect the electronics unit 48 to the computing device 16 such that the control signal, the measured impedance signal, and the EMG voltage signal are communicated through the cable. The system 10 functions in a substantially similar manner as discussed above.

In other embodiments, the electronics unit 48 also includes one or more wireless transceivers 50, as shown in FIG. 13. The wireless transceiver 50 may have features similar to the communication element 34 discussed above, such that the wireless transceivers are configured to transmit and receive data through ANT, ANT+, Bluetooth™, BLE, ISM, WiFi, cellular, etc. The electronics unit 48 may include a single transceiver to communicate the control signal, the measured impedance signal, and the EMG voltage signal to and from the computing device 16, or the electronics unit 48 may include one transceiver for each of the listed signals.

As noted above, it will be appreciated that the electronics unit 48, including the EBI unit 12, the EMG unit 14, and the wireless transceiver 50, as shown in FIG. 13 is implemented in a stand-alone fashion, independent of, and not retained by, the article of clothing 46. And the electronics unit 48 may function as described below, without the article of clothing 46.

In some embodiments, the electronics unit 48 communicates the measured impedance signal and the EMG voltage signal to a base station 52, which serves as a signal repeater and communicates the measured impedance signal and the EMG voltage signal to the computing device 16. In other embodiments, the electronics unit 48 communicates the measured impedance signal and the EMG voltage signal directly to the computing device 16. In either situation, the computing device 16 performs data calculations and determines when a bowel event is about to occur, as described above. When the processing element 38 determines that a bowel event is about to occur, it may provide an indication of the event such as by activating a light, sounding an alarm, or sending a notification to a smart phone or other mobile electronic device, activating a smart wearable electronic device, such as a watch or glasses, or an implanted electronic device, etc.

In certain embodiments, the computing device 16 may be embodied by, or included in, a mobile electronic device 54, exemplified by a smart phone, a wearable smart device, an implanted smart device, or other device. The electronics unit 48 communicates the measured impedance signal and the EMG voltage signal to the mobile electronic device 54 which performs data calculations and determines when a bowel event is about to occur, as described above. When the mobile electronic device 54 determines that a bowel event is about to occur, it may provide an indication of the event such as by vibrating, playing a ringtone or audible alert, displaying a message or notification on the screen, or combinations thereof.

In still other embodiments, the electronics unit 48 further includes the computing device 16, which makes the system 10 self-contained or stand-alone in the article of clothing 46. The system 10 determines when a bowel event is about to occur, as described above. When the system 10 determines that a bowel event is about to occur, it may provide an indication of the event such as by sending a notification to a smart phone or by sending a notification to another device which can activate a light, sound an alarm, or the like.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

EMG detects electrical activity of skeletal muscles, while EBI measures internal resistance of various biological tissues to the flow of electrical currents. A controlled amount of current is applied into a section of tissue through the current electrodes 22, and the resulting voltage across that tissue provides a detectable signal for recording and subsequent analysis. Any change in internal configuration such as density, material content, fluid conductivity, or conformation, is detected through the change in the detected voltage. Information regarding the amount of applied current, voltage measurement, and phase angle permits characterization of an impedance profile for that tissue region. Alternating current (AC) is typically used for the source of the electrical current in impedance measurements.

In this example, EBI and EMG measurements via surface electrodes 22, 24, 32 were used in a non-invasive configuration to assess the descendent colon and rectum motility. Body movement artifacts were analyzed to discriminate from intrinsic bowel activity. Fixed alternating current of less than 1 mA and of 50 kHz frequency was applied to the pelvic region in a configuration meant to maximize generation of equipotential line/electrical field across the rectum. This preliminary, preclinical study included measurements at rest in a semi-recumbent position, and during hip flexion, external stomach pressure, bearing down, and ingestion of a stimulant laxative medication. Analysis of the EMG signal, impedance Z, and the derivation of the impedance (dZ/dT) was performed by filtering, averaging and variability analysis, considering averaging and standard deviation (SD) for discrete periods. Results support the conceptual framework of colorectal electrical bioimpedance, and demonstrate differences between EMG and EBI activity under various conditions.

In the protocol, current electrodes 22 were used to create an electrical field centered over the colon of a subject, while voltage electrodes 24 were used to detect changes in that electrical field. In this configuration, four electrodes 22 were used to generate the electrical field (four outer current-generating electrodes), and four inner voltage-detecting electrodes 24 were used to detect changes, as illustrated in FIG. 10. Two additional EMG electrodes 32 were placed in the extreme of one of the impedance electrode lines to detect the EMG signal (FIG. 10). The article of clothing 46 was used to maintain electrode 22, 24, 32 positioning, and avoid release due to skin flexion during normal movements. The electrodes 22, 24 are attached to a power source and a receiver/monitor to receive the output signal. A BIOPAC Systems MP160 with ACQKnowledge 5 software (BIOPAC Systems, Goleta Calif.), including the EMG2-R and NICO-R BioNomadix Cardiac Output modules, was adapted for generating the current and measuring the electrical signals.

A small current (<1 mA) is output across the colorectal area of the subject to create the electrical field, centered over the colon. The voltage generated along the colon area of the body is then detected by the detecting electrodes 24 and transmitted to the receiver, and changes in the voltage are determined which correspond to a signal of bioimpedance in the colon. Muscle movement is also detected and transmitted by the EMG electrodes 32 to the receiver.

Impedance Z and EMG measurements were taken over time and under different conditions as follows:

Five minutes were recorded at rest in semi-fowler position in order to observe the internal natural noise for this configuration (respiration, upper colon motility, muscle involuntary movements etc.);

Five minutes with alternating leg lifting every 15 seconds. The movements last for 4 seconds (two for lifting, and two for restoring position). The purpose of this step is to observe the changes due to natural leg movements;

Five minutes with voluntary abdominal pressing every 15 seconds without mechanical help. Each pressing event last for 4 seconds. This gives the effect of deep respirations, for example;

Five minutes with internal pushing (as if need to evacuate) every 15 seconds. This step is to discriminate the voluntary attempt to evacuate from the involuntary reaction of the muscles to promote the evacuation;

Administration of a laxative medication, followed by one hour completely at rest to observe the effects of the medication on the electrical and motility activity in the region.

Analysis of the EMG signal, impedance Z and the derivation of the impedance (dZ/dT) is performed by filtering, averaging and variability analysis, considering averaging ($\bar{X}$) and standard deviation (SD) for periods of 0.5 second and overlapping of (N−1) points. This means a smoothing of the signal by averaging and getting variability by SD data also smoothed by the overlapping. Correlation of the average and variability data among the three signals were performed.

A sample of each signal with the events described in the methodology are shown in FIGS. 14A-14E. Averaging and SD data were considered for correlation analysis among signals (EMG, Z, dZ/dT) as described above. It was expected that the biggest correlations appear for Z vs dZ/dT for obvious reasons. The purpose of the resting (basal) stage is to observe if the electrode 22, 24, 32 configuration is sensitive to other internal movements. No big correlations were found among impedance data (Z or dZ/dT) and EMG in this basal stage. The other three steps, corresponding to induced disturbances, show clear correlations among signals with differences in intensity and particular noise level (Table 1).

TABLE 1

Correlations among the signals (three different pairs of signals) for averaging and SD data

|  | EMG vs Z | | EMG vs dZ/dT | | Z vs dZ/dT | |
| --- | --- | --- | --- | --- | --- | --- |
|  | $\bar{X}$ | SD | $\bar{X}$ | SD | $\bar{X}$ | SD |
| Resting | 0.05 | 0.04 | −0.04 | −0.01 | 0.63 | 0.55 |
| Leg lifting | 0.24 | 0.24 | 0.44 | 0.43 | 0.59 | 0.63 |
| Stomach pressing | 0.34 | 0.33 | 0.24 | 0.25 | 0.58 | 0.63 |

TABLE 1-continued

Correlations among the signals (three different pairs of signals) for averaging and SD data

|  | EMG vs Z | | EMG vs dZ/dT | | Z vs dZ/dT | |
| --- | --- | --- | --- | --- | --- | --- |
|  | $\bar{X}$ | SD | $\bar{X}$ | SD | $\bar{X}$ | SD |
| Internal pushing | 0.84 | 0.86 | 0.51 | 0.54 | 0.62 | 0.65 |
| Medication | 0.71 | 0.78 | 0.24 | 0.29 | 0.41 | 0.43 |

For internal pushing and the events due to medication (laxative), the correlations among EMG and impedance (Z) is high enough and statistically significant to be considered as a potential discriminator of such events. In the case of medication, the correlation between Z and dZ/dT is the lowest. This last result means that the Z signal is noisier in this case than in the others because of the medication's effects. This indicates that the system 10 may also be useful for pharmacodynamics analysis for a variety of different medications.

Example 2

The system 10 was used while the subject carried out various activities to monitor and discern colon activity. As described in Example 1, EMG (muscle activity), Impedance (Z, internal electrical resistance), and changes in impedance (dZ/dT) were measured with the system 10. The correlation (R) among these three signals is indicative of colonic activity. The system 10 records and analyzes impedance Z and EMG signals to identify distinct patterns under different physiologic conditions. These conditions include rest, skeletal muscle movement (abdominal and upper leg), bear down maneuver, and intrinsic/involuntary colonic contraction.

Figure 15:
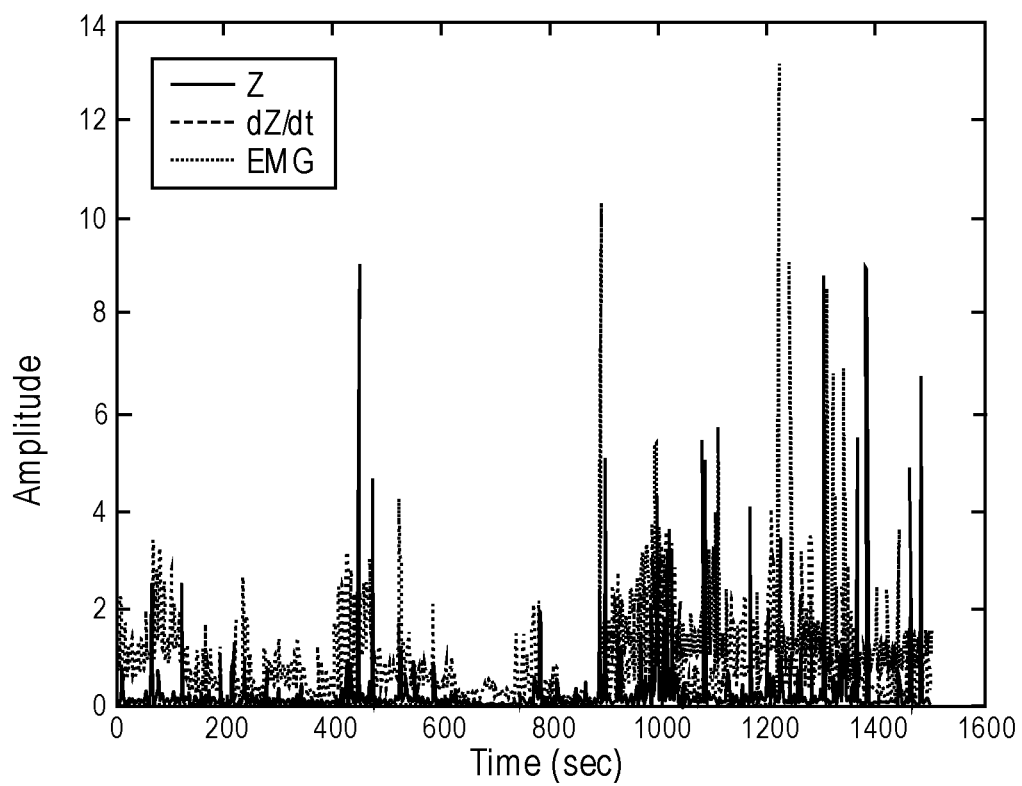
FIG. 15 is a plot of amplitude versus time for the impedance Z measurement, a derivative dZ/dt, and a measurement of EMG voltage after the subject has eaten a breakfast comprising yogurt and fruit.
Figure 16:
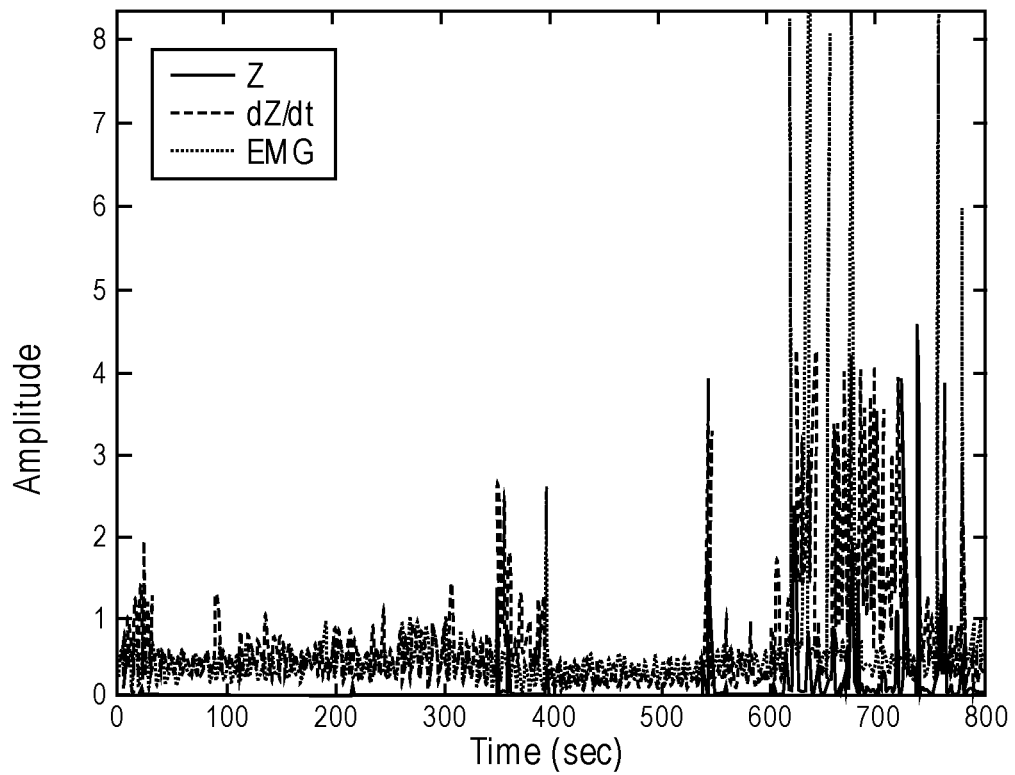
FIG. 16 is a plot of amplitude versus time for the impedance Z measurement, a derivative dZ/dt, and a measurement of EMG voltage after the subject has ingested chocolate milk.

The subject consumed a normal breakfast of yogurt with fruit, and the system 10 was used to gather measurements at least 4 hours later. The subject was monitored during 15 minutes at rest lying in bed, followed by 5 minutes of active "pushing" for 4 seconds with 20-second intervals. The data is shown in FIG. 15. After the resting period, the subject consumed 473 ml chocolate milk, followed, after 12 minutes, by pushing for 3 minutes in 20-second intervals. Similar results were obtained. The results are shown in FIG. 16.

In another session, one day after, having taken the same breakfast at least four hours before the test, the subject consumed 296 ml of cold fruit juice. The subject was seated. The results are shown in FIG. 17.

The main outcomes observed in these tests are as follows. Relaxing inhibits myoelectrical activity, but internal pushing triggers this activity not only during pushing event, that is, it triggers an apparent "awakening of the colon". False positives (of real colon activity) are observed in the case of voluntary movement of the pelvis and mainly the rectum, as well as involuntary movements, such as hiccups. Other events like sighs are clearly discriminated because dZ/dT event does not correspond to any EMG activity. Movements from thigh or arm have EMG event but do not have dZ/dT corresponding event. The correlation of impedance (or dZ/dT) event with EMG could be seen immediately or as a deferred effect (impedance changes after EMG activity event). Also, we observed some events with dZ/dT spikes corresponding with changes in an apparent continuous EMG noise patterns. In a situation of evacuation urgency, periodic sensations and EMG events (with the corresponding Z events) are recorded, with an increase of continuous activity when time passes and therefore, fulness sensation increases.

EMG activity is observed without sensation, but all sensations are related with impedance changes. EMG-dZ/dT correlations are also observed without any sensation (seems to be the case of very small and weak colon activity). The correlations among the signals are good if we focus the analysis to the regions of interest (discarding movement artifacts and periods without evident events, just with noise). In fact, the best correlations are between EMG and dZ/dT signals.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

The invention claimed is:

1. A non-invasive colon motility monitoring system comprising:
    an electrobioimpedance unit configured to measure an impedance of a body of a subject in a colorectal region and communicate an impedance signal that varies according to the measured impedance;
    an electromyography unit configured to measure an electric voltage of the body of the subject in the colorectal region and communicate a voltage signal that varies according to the measured voltage; and
    a computing device including a processing element in electronic communication with a memory element, the processing element configured or programmed to:
        receive the impedance signal and determine impedance data from the impedance signal,
        receive the voltage signal and determine voltage data from the voltage signal,
        compute impedance derivative data from the impedance data,
        compute a correlation between any two of the impedance data, the voltage data, and the impedance derivative data, and
        provide an indication of when a bowel event is about to occur based on the correlation.

2. The non-invasive colon motility monitoring system of claim 1, wherein the electrobioimpedance unit includes
    an electric current source configured to inject electric current,
    an electric voltage meter configured to measure electric voltage,
    a plurality of current electrodes coupled to the electric current source, and
    a plurality of voltage electrodes coupled to the electric voltage meter,
    wherein a first current electrode and a second current electrode are configured to be positioned spaced apart from one another; and
    wherein a first voltage electrode and a second voltage electrode are configured to be positioned spaced apart from one another and between the first current electrode and the second current electrode.

3. The non-invasive colon motility monitoring system of claim 2, wherein the current electrodes are utilized to inject electric current in a plurality of locations and the voltage electrodes are utilized to measure electric voltage near the same locations and the impedance signal varies according to an average of the measured impedance of the region bounded by the locations of the current electrodes and the voltage electrodes.

4. The non-invasive colon motility monitoring system of claim 2, wherein the electrobioimpedance unit includes four current electrodes and four voltage electrodes and the four current electrodes are configured to be positioned to form a first quadrilateral and the four voltage electrodes are configured to be positioned to form a second quadrilateral that is smaller in one dimension than the first quadrilateral and located within the first quadrilateral such that a first pair of current electrodes is aligned with a first pair of voltage electrodes and a second pair of current electrodes is aligned with a second pair of voltage electrodes.

5. The non-invasive colon motility monitoring system of claim 4, wherein:
    the first pair of current electrodes and the first pair of voltage electrodes form a first impedance measurement group that is vertically oriented and the second pair of current electrodes and the second pair of voltage electrodes form a second impedance measurement group that is vertically oriented,
    the first impedance measurement group is configured to be positioned on the left side of the body of the subject along a line between the ischial spine and coccyx and the second impedance measurement group is configured to be positioned on the right side of the body of the subject along a line between the ischial spine and coccyx, and
    the first quadrilateral is positioned in the colorectal region.

6. The non-invasive colon motility monitoring system of claim 5, wherein the electromyography (EMG) unit includes an electric voltage meter configured to measure electric voltage and a plurality of EMG electrodes coupled to the electric voltage meter, wherein first and second EMG electrodes are configured to be positioned in alignment with either the first impedance measurement group or the second impedance measurement group such that each EMG electrode is positioned at an opposing end of either impedance measurement group.

7. The non-invasive colon motility monitoring system of claim 6, wherein the electromyography (EMG) unit includes a third EMG electrode configured to be positioned in the vicinity of either the first or second EMG electrodes.

8. The non-invasive colon motility monitoring system of claim 1, wherein the processing element is further configured or programmed to compute a correlation between the impedance data and the voltage data and determine that a bowel event is about to occur when the correlation is greater than a threshold value.

9. The non-invasive colon motility monitoring system of claim 1, further comprising a communication element configured to wirelessly communicate the impedance signal and the voltage signal to the computing device.

10. The non-invasive colon motility monitoring system of claim 1, further comprising an article of clothing retaining the electrobioimpedance unit and the electromyography unit, the article of clothing configured to be worn to cover the colorectal region of the subject.

11. The non-invasive colon motility monitoring system of claim 10, wherein the article of clothing further retains the computing device and the non-invasive colon motility monitoring system further comprises a wireless transceiver configured to wirelessly communicate the indication of the bowel event.

12. The non-invasive colon motility monitoring system of claim 10, wherein the electrobioimpedance unit includes four current electrodes and four voltage electrodes and the four current electrodes are configured in the article of clothing to be positioned to form a first quadrilateral and the four voltage electrodes are configured in the article of clothing to be positioned to form a second quadrilateral that is smaller in one dimension than the first quadrilateral and located within the first quadrilateral such that a first pair of current electrodes is aligned with a first pair of voltage electrodes and a second pair of current electrodes is aligned with a second pair of voltage electrodes.

13. The non-invasive colon motility monitoring system of claim 12, wherein
the first pair of current electrodes and the first pair of voltage electrodes form a first impedance measurement group that is vertically oriented and the second pair of current electrodes and the second pair of voltage electrodes form a second impedance measurement group that is vertically oriented,
the first impedance measurement group is configured to be positioned on the left side of the body of the subject along a line between the ischial spine and coccyx and the second impedance measurement group is configured to be positioned on the right side of the body of the subject along a line between the ischial spine and coccyx, and
the first quadrilateral is positioned in the colorectal region of the subject when the article of clothing is worn by the subject.

14. The non-invasive colon motility monitoring system of claim 13, wherein the electromyography (EMG) unit includes an electric voltage meter configured to measure electric voltage and a plurality of EMG electrodes coupled to the electric voltage meter, wherein first and second EMG electrodes are configured to be positioned in alignment with either the first impedance measurement group or the second impedance measurement group such that each EMG electrode is positioned at an opposing end of either impedance measurement group in the article of clothing.

15. The non-invasive colon motility monitoring system of claim 14, wherein the article of clothing retains the current electrodes, the voltage electrodes, and the EMG electrodes within a fabric that forms at least a portion of the article of clothing.

16. The non-invasive colon motility monitoring system of claim 10, wherein the processing element is further configured or programmed to compute a correlation between the impedance data and the voltage data and determine that a bowel event is about to occur when the correlation is greater than a threshold value.

\* \* \* \* \*